(12) United States Patent
Abbott et al.

(10) Patent No.: US 9,656,058 B2
(45) Date of Patent: May 23, 2017

(54) COCHLEAR IMPLANT INSERTION METHOD AND SYSTEM

(75) Inventors: Jacob J. Abbott, Salt Lake City, UT (US); James R. Clark, Salt Lake City, UT (US); Frank M. Warren, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 316 days.

(21) Appl. No.: 13/579,835

(22) PCT Filed: Feb. 14, 2011

(86) PCT No.: PCT/US2011/024754
§ 371 (c)(1),
(2), (4) Date: Jan. 29, 2013

(87) PCT Pub. No.: WO2011/103059
PCT Pub. Date: Aug. 25, 2011

(65) Prior Publication Data
US 2013/0138117 A1 May 30, 2013

Related U.S. Application Data

(60) Provisional application No. 61/305,294, filed on Feb. 17, 2010.

(51) Int. Cl.
*A61B 34/00* (2016.01)
*A61N 1/05* (2006.01)
*A61B 17/00* (2006.01)

(52) U.S. Cl.
CPC ............ *A61N 1/0541* (2013.01); *A61B 34/70* (2016.02); *A61B 2017/00787* (2013.01); *A61B 2034/731* (2016.02)

(58) Field of Classification Search
CPC .......... A61B 19/22; A61B 2017/00787; A61B 2019/2257; A61B 1/00158; A61B 34/73; A61B 2034/731; A61B 34/20; A61B 2034/251; A61N 1/0541; A61F 2002/6863; A61F 2002/30079
USPC .................................... 606/130, 129; 600/12
See application file for complete search history.

(56) References Cited

U.S. PATENT DOCUMENTS

| | | | | |
|---|---|---|---|---|
| 5,125,888 A | * | 6/1992 | Howard et al. | 600/12 |
| 5,931,818 A | * | 8/1999 | Werp et al. | 604/270 |
| 6,157,853 A | * | 12/2000 | Blume | A61B 19/22 |
| | | | | 600/426 |
| 6,216,026 B1 | * | 4/2001 | Kuhn et al. | 600/409 |

(Continued)

OTHER PUBLICATIONS

Adunka, et al.; "Impact of electrode insertion depth on intracochlear trauma"; Otolaryngology—Head and Neck Surgery; vol. 135, pp. 374-382, 2006.

(Continued)

*Primary Examiner* — Eric Rosen
*Assistant Examiner* — Chima Igboko
(74) *Attorney, Agent, or Firm* — Thorpe North & Western, LLP

(57) ABSTRACT

Techniques for insertion of a cochlear implant include using a rotatable manipulator magnet to steer the tip of the cochlear implant. Steering can use magnetic torque and/or force between the manipulator magnet and a magnetic element coupled to the tip of the cochlear implant to control bending of the cochlear implant.

18 Claims, 5 Drawing Sheets

(56) References Cited

U.S. PATENT DOCUMENTS

| | | | |
|---|---|---|---|
| 6,272,370 B1* | 8/2001 | Gillies et al. | 600/411 |
| 6,358,281 B1 | 3/2002 | Berrang et al. | |
| 6,375,606 B1* | 4/2002 | Garibaldi et al. | 600/12 |
| 6,651,665 B1* | 11/2003 | Sellers et al. | 128/207.14 |
| 6,817,364 B2 | 11/2004 | Garibaldi et al. | |
| 7,066,924 B1* | 6/2006 | Garibaldi et al. | 604/510 |
| 7,305,263 B2* | 12/2007 | Creighton, IV | 600/424 |
| 7,625,382 B2* | 12/2009 | Werp et al. | 606/108 |
| 2004/0249262 A1* | 12/2004 | Werp et al. | 600/411 |
| 2005/0187424 A1* | 8/2005 | Hambuchen et al. | 600/12 |
| 2006/0052656 A1* | 3/2006 | Maghribi et al. | 600/12 |
| 2007/0225787 A1* | 9/2007 | Simaan | A61N 1/0541 607/137 |
| 2009/0005836 A1* | 1/2009 | Chang et al. | 607/57 |
| 2009/0105579 A1* | 4/2009 | Garibaldi | 600/409 |
| 2009/0216296 A1 | 8/2009 | Meskens | |
| 2009/0231073 A1* | 9/2009 | Horisaka | A61B 1/041 335/209 |
| 2009/0306458 A1 | 12/2009 | Parker et al. | |
| 2010/0125311 A1* | 5/2010 | Choi et al. | 607/45 |

OTHER PUBLICATIONS

Balkany, et al.; "Modiolar proximity of three perimodiolar cochlear implant electrodes"; Act Oltolaryngol, vol. 122, pp. 363-369, 2002.

Bell, et al.; "A flexible micromachined electrode array for cochlear prosthesis"; Sensors and Actuators A, vol. 66:63-69, 1998.

Bhatti ; et al.; "A 32-site 4-channel high-density electrode array for a cochlear prosthesis"; IEEE J. of Solid-State Circuits, 1:2965-2973; 2006.

Bhatti, et al.; "A high-density electrode array for a cochlear prosthesis"; Proc. Int. Conf. on Solid-State Sensors, Actuators and Microsystems; vol. 2, pp. 1750-1753, 2003.

Gstoettner, et al.; "Perimodiolar electrodes in cochlear implant surgery"; Acta Oltolaryngol, vol. 121 216-219, 2001.

Judy, et al.; "Magnetic microactuation of polysilicon flexure structures"; J. of Microelectromechanical Systems, vol. 4, pp. 162-169, 1995.

Kha, et al.; "Determination of frictional conditions between electrode array and endosteum lining for use in cochlear implant models"; J. of Biomechanics, vol. 39, 1752-1756; 2006.

Mirzadeh, et al.; "Segmented detachable structure of cochlear-implant, electrodes for clochlear-implant electrodes for close-hugging engagement with the modiolus"; J. of Biomedical Materials Research, vol. 68B, pp. 191-198, 2004.

Rebscher, et al.; "Considerations for design of future cochlear implant electrode arrays: Electrode array stiffness, size, and depth of insertion"; J. of Rehabilitation Research and Development, vol. 45 pp. 731-718, 2008.

Roland, Jr.; "A model for cochlear implant electrode insertion and force evaluation: Results with a new electrode design and insertion technique"; The Laryngoscope, vol. 115, pp. 1325-1338, 2005.

Tang, et al.; "Technology and integration of poly-crystalline diamond piezoresistive position sensor for cochlear implant probe"; Proc. Int. Conf. on Solid-State Sensors, Actuators and Microsystems; vol. 1, pp. 543-546, 2005.

Todd, et al.; "Force application during cochlear implant insertion: An analysis for improvement of surgeon technique"; IEEE Trans. on Biomedical Engineering, vol. 54, pp. 1247-1255; 2007.

Tunay, "Modeling magnetic catheters in external fields"; IEEE Proc. Proceedings of the $26^{th}$ Annual International Conference of the IEEE EMBS, 2004; vol. 1; pp. 2006-2009.

Tunay; "Position Control of Catheters Using Magnetic Fields"; IEEE 2004; pp. 392-397.

Wang, et al.; "A cochlear electrode array with built-in position sensing"; Proc. Int. Conf. on Micro Electro Mechanical Systems, pp. 786-789, 2005.

Wang, et al.; "A parylene-silicon cochlear electrode array with integrated position sensors"; IEEE Proc. EMBS Annual Int. Conf.; pp. 3170-3173, 2006.

Wu, et al.; "A curvature-controlled 3d micro-electrode array for cochlear implants"; Proc. Int. Conf. on Solid-State Sensors, Actuators and Microsystems; vol. 2, pp. 1636-1639, 2005.

Yoo, et al.; "Three-dimensional modeling and visualization of the cochlea on the internet"; IEEE Trans. on Information Technology in Biomedicine, vol. 4(2), pp. 144-151; 2000.

Zhang, et al.; "Model and Parameter Identificaton of Friction durig Robotic Insertion of Cochlear-Implant Electrode Arrays"; Int. Conf. on Robotics & Automation; IEEE 2009; 6 pages.

Zhang, et al.; "A pilot study of robot-assisted cochlear implant surgery using steerable electrode arrays"; Proc. MICCAI Medical Image Computing and Computer-Assisted Intervention, vol. 4190, 2006; 8 pages.

Zhang, et al.; "Optimal path planning for robotic insertion of steerable electrode arrays in cochlear implant surgery"; ASME Trans. Journal of Medical Devices, 3 (011001), 2009; 10 pages.

Zhang, et al.; "Path planning and workspace determination for robot-assisted insertion of steerable electrode arrays for cochlear implant surgery"; Proc. MICCAI Medical Image Computing and Computer-Assisted Intervention, vol. 5242; 2008; 9 pages.

International Search Report and Written Opinion issued for PCT/US2011/024754. dated Oct. 24, 2011. 10 pages.

* cited by examiner

COCHLEAR IMPLANT INSERTION METHOD AND SYSTEM

This application claims the benefit of U.S. Provisional Patent Application Ser. No. 61/305,294, filed on Feb. 17, 2010, and incorporated herein by reference.

FIELD

The present application relates to cochlear implants. More particularly, the present application relates to systems and methods for insertion of a cochlear implant electrode array into a cochlea using magnetic steering.

BACKGROUND

Cochlear implant systems have been of great benefit to some people with hearing loss. The electrode array (hereafter referred to simply as "the cochlear implant") portion of the cochlear implant system is inserted into the scala-tympani chamber of the spiral-shaped cochlea. This positions electrodes of the cochlear implant near nerves within the cochlea responsible for hearing. An external portion of the cochlear implant system picks up sound in the environment and communicates with the cochlear implant electrodes. The electrodes stimulate the nerves to create the perception of sound.

Performance of a cochlear implant system is, in part, a function of how close the electrodes are positioned relative to the nerve cells and how far into the cochlea the cochlear implant has been inserted. Because of the spiral nature of the cochlea, insertion of the cochlear implant is difficult without causing damage to delicate structures within the cochlea. For example, damage to the cochlea can be caused by scraping or puncturing of the walls of the cochlea. Unintended motions of the implant, including for example folding or buckling of the implant, can also occur. Damage can result in loss of residual hearing as well as a decrease in the effectiveness of the implant.

BRIEF DESCRIPTION OF THE DRAWINGS

Additional features and advantages of the invention will be apparent from the detailed description that follows, taken in conjunction with the accompanying drawings, that together illustrate, by way of example, features of the invention; and, wherein.

DETAILED DESCRIPTION

Figure 1:
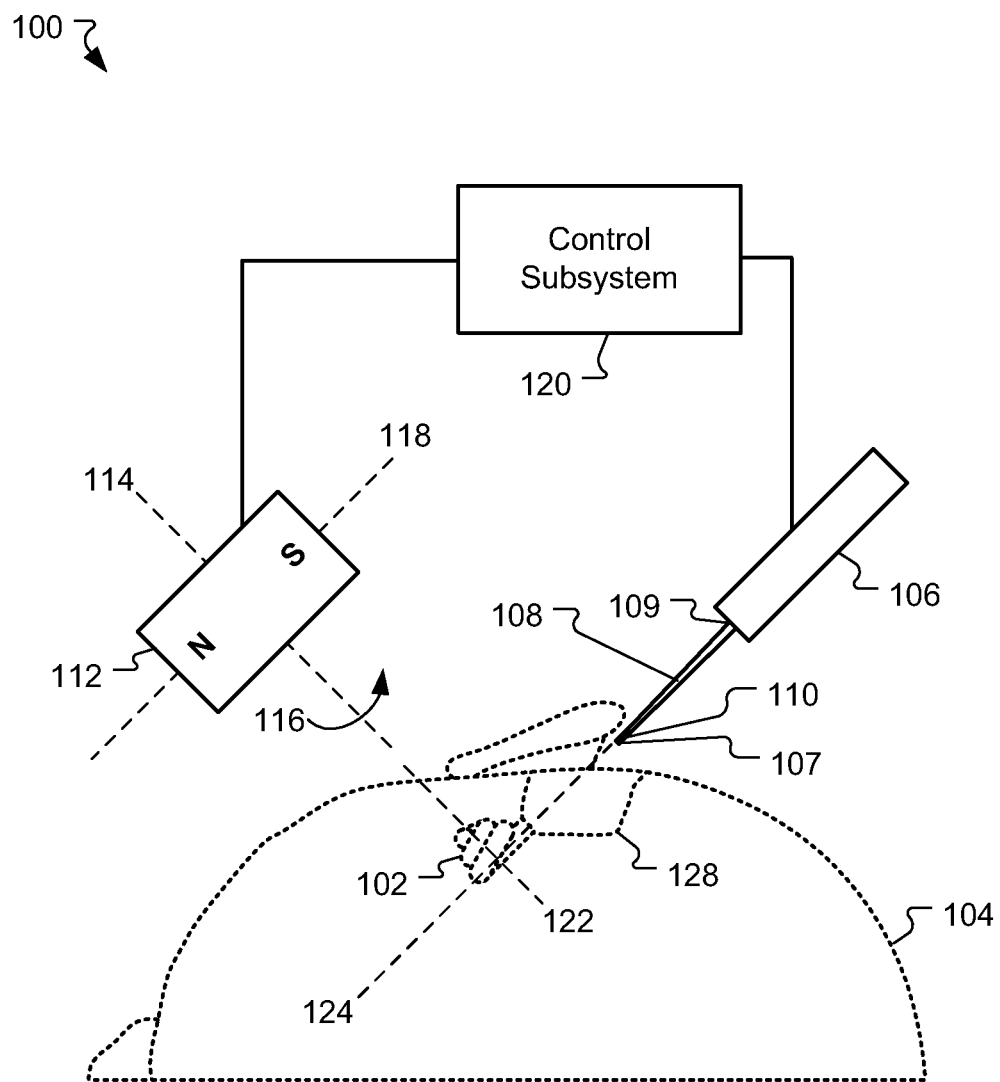
FIG. 1 is a schematic block diagram showing a system for insertion of a cochlear implant being used to insert a cochlear implant into a patient in accordance with some embodiments of the present invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

In describing the present invention, the following terminology will be used:

The singular forms "a," "an," and "the" include plural referents unless the context clearly dictates otherwise. Thus, for example, reference to an item includes reference to one or more of the items.

As used herein, the term "about" means quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art.

By the term "substantially" is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all the individual numerical values or sub-ranges encompassed within that range as if each numerical value and sub-range is explicitly recited. As an illustration, a numerical range of "about 1 to 5" should be interpreted to include not only the explicitly recited values of about 1 to 5, but also include individual values and sub-ranges within the indicated range. Thus, included in this numerical range are individual values such as 2, 3, and 4 and sub-ranges such as 1-3, 2-4, and 3-5, etc. This same principle applies to ranges reciting only one numerical value and should apply regardless of the breadth of the range or the characteristics being described.

As used herein, a plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items.

As used herein, the term "alternatively" refers to selection of one of two or more alternatives, and is not intended to limit the selection to only those listed alternatives unless the context clearly indicates otherwise.

As used herein, the term "magnetic axis" refers to an axis drawn through the poles of a magnet or magnetic field. For example, the magnetic axis of a magnet can be a line passing through the north pole and the south pole of the magnet.

As used herein, the term "magnetic torque" refers to interaction between magnets and magnetic fields that produces or tends to produce torsion or rotation of an object. Magnetic torque can be measured in units of Newton-meters (Nm). Magnetic torque between two magnets is, in part, of function of the relative angle of the magnetic axes of the magnets.

As used herein, the term "magnetic force" refers to interaction between magnets and magnetic fields that produces or tends to produce linear acceleration or movement of an object. Magnetic force can be measured in units of Newtons (N). Magnetic force between two magnets is, in part, a function of the gradient of the magnetic field of one magnet in the vicinity of the other magnet.

As disclosed herein, a relatively simple magnetic control system has been developed that can be used to help steer a cochlear implant during insertion. The cochlear implant can include a magnetic element near its tip. The magnetic element can be, for example, a permanent magnet. As another example, the magnetic element can be a magnetic material that is magnetized in response to a magnetic field. As another example, the magnetic element can be an electromagnet (e.g., a coil having electrical connections through the cochlear implant to allow a current to be passed through the coil).

Magnetic force and torque can be applied to the magnetic element of the cochlear implant to control bending of the cochlear implant as it is inserted. As one example, a pre-curved cochlear implant can be initially straightened by application of appropriate magnetic forces to the magnetic element, and then allowed to return to its curved shape as it is being inserted. As another example, a straight cochlear implant can be forced to curve while it is being inserted by application of magnetic forces to the magnetic element. In some embodiments, bending can be controlled by magnetic torque, while magnetic forces (e.g., due to magnetic field gradients when using a localized magnetic source) can be minimized by maintaining the axis of the magnetic field of a control element approximately perpendicular to the axis of the magnetic field of the magnetic element of the implant. Magnetic steering of the cochlear implant during insertion can provide benefits such as reduced insertion force, reduced trauma, deeper insertion, and closer proximity to the modiolar wall (i.e., the inner wall of the cochlear spiral).

Turning to FIG. 1, a system for insertion of a cochlear implant is illustrated in accordance with some embodiments of the present invention. The system, shown generally at 100, can be used to insert a cochlear implant 108 into a cochlea 102, such as for example, the cochlea of a living human patient 104. The system can include a positioning means for linearly positioning the cochlear implant. For example, the system can include a positioner 106 which provides for linear movement and positioning of the cochlear implant. The cochlear implant can be removably attached at one end 109 to the positioner. For example, the positioner can include a clamping mechanism or other element to allow for holding the cochlear implant during insertion and release of the cochlear implant when insertion is complete. The positioner can allow for translation (movement) of the cochlear implant in a direction aligned with the longitudinal axis of the cochlear implant. Disposed at or near the other end of the cochlear implant can be a magnetic element 110. The magnetic element can have a magnetic axis 124 which can be aligned with the longitudinal axis of the cochlear implant (e.g., the north pole or the south pole of the magnetic element can be disposed at the tip 107 of the cochlear implant). Alternatively, the magnetic axis can be aligned differently with respect to the cochlear implant.

The system can also include a source means for generating a rotatable magnetic field. For example, a rotatable manipulator magnet 112 can provide a magnetic field that originates from a localized source. For example, the manipulator magnet can be rotatable in a direction 116 about a rotation axis 114 perpendicular to the manipulator magnet's magnetic axis 118. In use, the rotation axis can be substantially parallel and aligned with a spiral axis 122 of the cochlea as discussed further below.

Various types of magnets can be used for the rotatable manipulator magnet 112, including for example, a permanent magnet and an electromagnet. Various rotation means for providing the rotation can be used, including for example, coupling the manipulator magnet to a motor or any suitable element capable of providing controlled rotary motion. As another example, a rotatable manipulator magnet can be an electromagnet wherein electronically varying the current amount and direction allows for controlled rotation of the magnetic field.

The system 100 can also include a control subsystem 120 coupled to the positioner 106 and the rotatable manipulator magnet 112 through control interfaces (e.g., servo loops, robotic command interfaces, and the like). The control subsystem can be used to coordinate linear movement of the cochlear implant 108 with rotation of the manipulator magnet during the insertion of the cochlear implant. For example, coordinated movement of the positioner and rotation of the manipulator magnet can allow the tip 107 of the cochlear implant to be magnetically steered around the spiral of the cochlea 102. Operation of the control subsystem will become apparent from the below description. The control subsystem can be implemented using hardware, software, or a combination thereof. Accordingly, the control subsystem can include a specialized or general purpose processor programmed to control operation of the positioner 106 and the rotatable manipulator magnet 112 as described below.

Control of the positioner 106 and rotatable manipulator magnet 112 can be coordinated by the control subsystem 120 to ensure that the magnetic element 110, and thus tip 107, of the cochlear implant 108 is at a desired angle as a function of the position of the tip of the cochlear implant. For example, the position of the tip can be determined in part as a function of the amount of linear displacement produced by the positioner. A predefined relation between the linear displacement and the desired angle of the tip can be defined based on any of the following: a model of typical cochlea geometry, a measurement of the patient's particular cochlea geometry, and combinations thereof. The control subsystem can thus use the predefined relation to control the angle of the manipulator magnet 112 as a function of the amount of linear advancement of the cochlear implant 108. For example, a table can be stored in a memory of the control subsystem, and the table can define a desired relationship between linear advancement values and desired angles of the tip. As another example, a predefined function can allow calculation of the desired angle as a function of the amount of linear advancement.

Steering of the cochlear implant 108 can be controlled using torque, magnetic force, or combinations of both. For example, maximum torque can be achieved when the magnetic axis 118 of the rotatable manipulator magnet 112 is approximately perpendicular to the magnetic axis 124 of the magnetic element 110. Maximum magnetic force can be achieved when the magnetic axis of the rotatable manipulator magnet is parallel with the magnetic axis of the magnetic element. Generally, lower insertion forces are expected when using maximum torque rather than magnetic force, as the magnetic force can cause the tip implant to press against cochlear walls and structures. In experiments, however, it has been observed that maximum force steering can sometimes provide lower insertion force than maximum torque steering. Both maximum force and maximum torque steering have been observed to provide reduced insertion forces as compared to insertion without magnetic steering.

In some embodiments, insertion of the cochlear implant 108 can proceed as follows. Preparation for insertion can include providing access to the cochlea, for example, through a surgical incision 128. The positioner 106 can be positioned proximate to the cochlea 102. The rotatable manipulator magnet 112 can also be positioned proximate to the cochlea. For example, the rotatable manipulator magnet can be positioned so that rotation axis 114 is substantially aligned with a spiral axis 122 of the cochlea. Perfect alignment is not necessary, and misalignment between the axes of less than 5 degrees, less than 10 degrees, or even less than 20 degrees may be tolerable.

Following this initial preparation, insertion can proceed as follows. The cochlear implant 108 can be advanced into the cochlea 102 using the positioner 106. Simultaneously with advancing the cochlear implant, the rotatable manipulator magnet 112 can be rotated to steer the tip of the cochlear implant. The magnetic field from the manipulator magnet can produce a magnetic torque on the magnetic element 110 which can control bending of the cochlear implant. For example, in some embodiments, a precurved cochlear implant can be used. Torque on the magnetic element can be used straighten the cochlear implant at the beginning of the insertion process, and then gradually reduced as the cochlear implant is inserted to allow the cochlear implant to return to its precurved shape providing a tight fit around the curved cochlea. In some embodiments, a substantially straight cochlear implant can be forced to bend by torque on the magnetic element. Accordingly, as the cochlear implant is advancing into the cochlea, rotating the manipulator magnet can cause the distal end of the cochlear implant to bend around the spiral axis 122 of the cochlea. In other words, the position of the manipulator magnet 112 (orientation of magnetic axis 118) can be controlled to produce a desired magnetic torque on the magnetic element 110 to position the tip 107 of the cochlear implant at a desired angle.

Figure 2A:
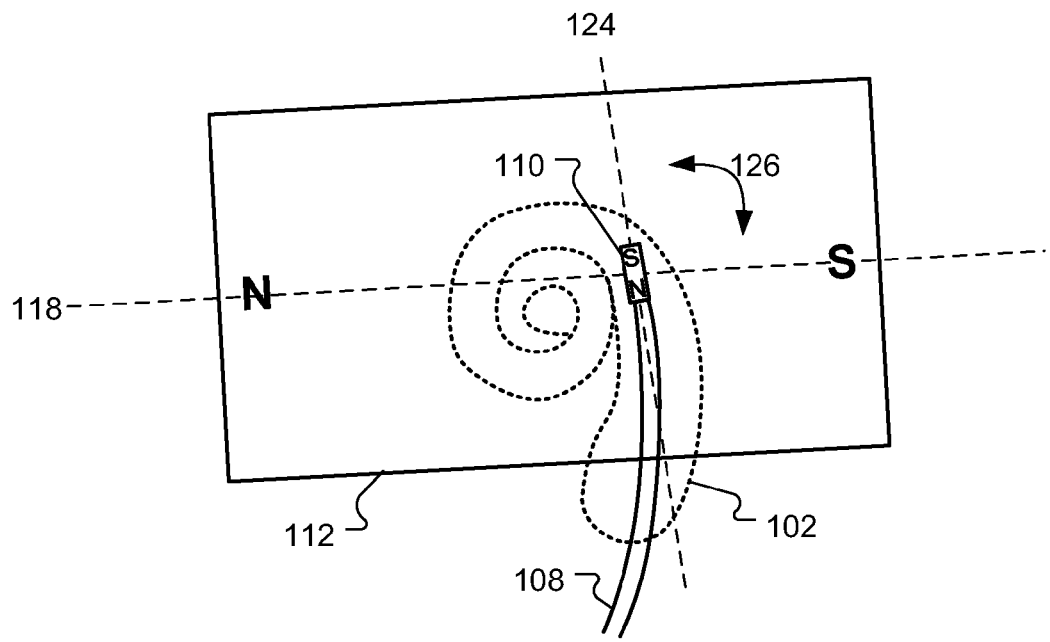
FIGS. 2(a)-2(c) are cross-sectional views viewed from a point aligned with the spiral axis of the cochlea showing positions of various elements during the process of inserting a cochlear implant into a patient in accordance with some embodiments of the present invention.
Figure 2C:
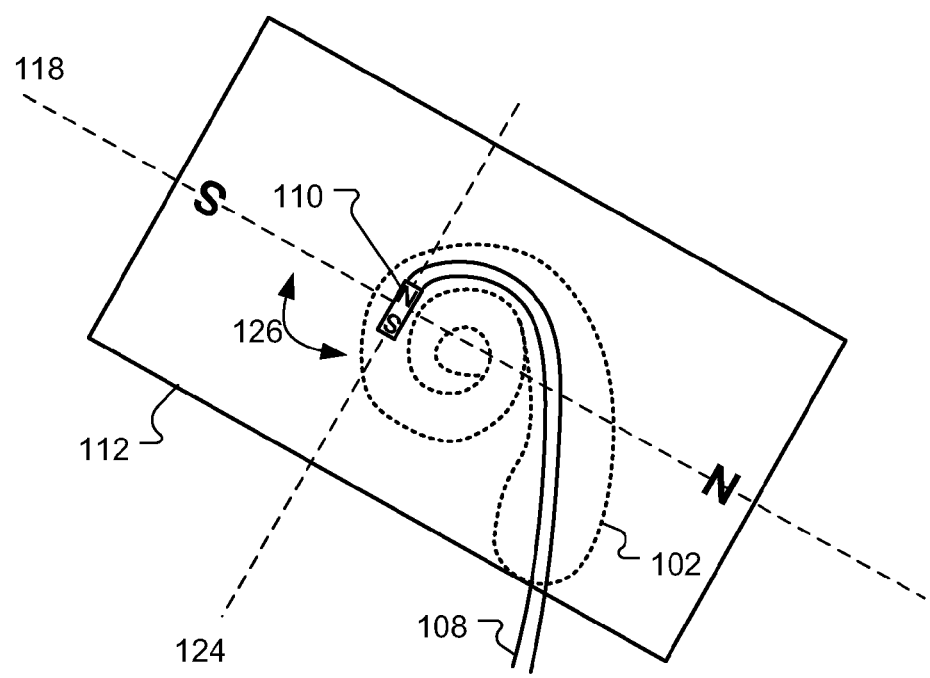
Figure 2B:
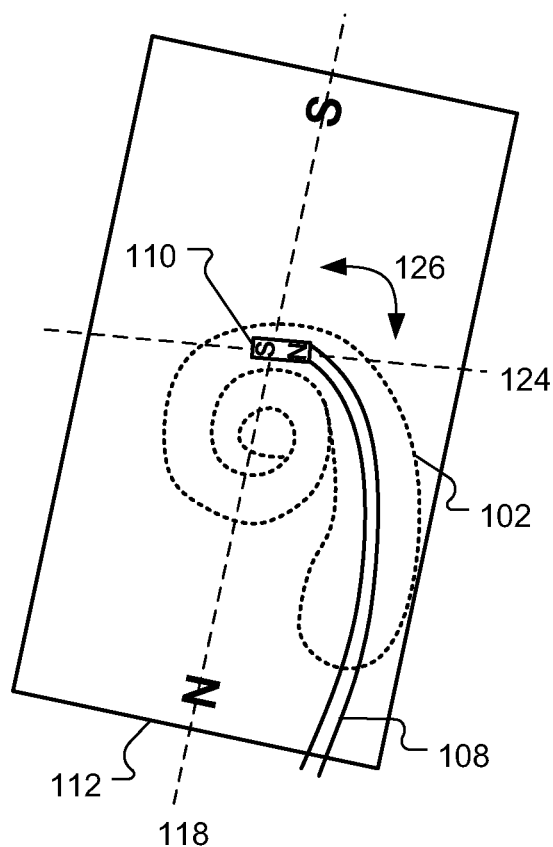

FIGS. 2(a)-2(c) illustrate several interim positions of the rotatable manipulator magnet 112 and cochlear implant 108 during the insertion process. It can be seen that, as the cochlear implant is advanced into the cochlea 102, the magnetic axis 118 of the manipulator magnet can be rotated so that it stays at a desired angle 126 (e.g., approximately orthogonal) relative to the magnetic axis 124 of the magnetic element 110 of the cochlear implant. For example, the angle between the axes can be kept at approximately 90 degrees or within some desired range of angles. It is not necessary to keep the angle perfectly constant during insertion, and deviations of less than 5 degrees, less than 10 degrees, or even less than 20 degrees may be tolerable.

As a particular example, the magnetic axis 118 of the manipulator magnet 112 can be maintained substantially orthogonal to the magnetic axis 124 of the magnetic element 110. With such an orientation, magnetic torque on the magnetic element caused by the magnetic field from the manipulator magnet can bend the tip of the cochlear implant in the correct direction to curve with the cochlear channel as it is inserted while undesirable forces between the manipulator magnet and the magnetic element can be minimized. Although FIG. 2(c) illustrates wrapping the cochlear implant around the spiral axis of approximately 180 degrees, it may be possible to provide sufficient insertion that the cochlear implant can be wrapped around the spiral axis by at least 360 degrees, at least 540 degrees, or about 810 degrees.

While the foregoing discussion has been described in terms of the rotatable manipulator magnet using physical rotation of a permanent magnet, an electromagnet or other magnetic field source can be used to generate a rotatable magnetic field. In general, rotating the magnetic axis 118 of the manipulator magnet can be performed mechanically (e.g., by physical rotation) or electronically (e.g., by varying currents within one or more electromagnets). Accordingly, references to the magnetic axis 118 can refer more generally to the magnetic axis of the rotatable magnetic field produced by the rotatable manipulator magnet.

Magnetic torque and magnetic force between the manipulator magnet 112 and the magnetic element 110 can be described as follows. In general, for a magnetic element having magnetization M (e.g., measured in units of Amperes/meter) and a volume v (e.g., measured in units of meters$^3$) the magnetic torque, T, and magnetic force, F, on the magnetic element can be approximated by:

$$T = vM \times B$$

$$F = v \begin{bmatrix} \frac{d}{dx}B^T \\ \frac{d}{dy}B^T \\ \frac{d}{dz}B^T \end{bmatrix} M$$

where B is the magnetic field (e.g., measured in units of Tesla) applied by the manipulator magnet, "x" is the vector cross-product operation, and superscript "T" indicates vector transpose. Magnetic torque can tend to align the magnetic element and tip of the cochlear implant with the applied magnetic field of the manipulator magnet. For example, magnetic torque produced on the magnetic element can be within the range of about 0.27 N-mm to about 58.8 N-mm.

Because the manipulator magnet can be a localized source of a magnetic field, the resulting magnetic field can have a non-uniform magnitude (gradient) in the vicinity of the cochlear implant. The gradient of the magnetic field in the vicinity of the magnetic element can result in magnetic force which can attract (or repel) the magnetic element and tip of the cochlear implant toward (or away) from the manipulator magnet. In other words, the non-uniformity of the magnetic field can cause magnetic forces on the magnetic element.

The magnetic forces can be controlled in several manners. First, by keeping the magnetic axis 118 of the manipulator magnet approximately perpendicular (orthogonal) to the magnetic axis 124 of the magnetic element, the force equation can be approximately zero, resulting in small or negligible magnetic force (e.g., a force less than a desired threshold). Second, to produce a given magnitude of magnetic field, a physically larger manipulator magnet placed at a distance farther from the cochlear implant can produce smaller field gradients.

For example, the magnetic force can be less than about 0.027 N

On the other hand, some magnetic force can prove beneficial in helping to guide the cochlear implant in light of the three dimensional nature of the cochlea. In particular, the cochlea not only spirals around the spiral axis 122, but also spirals upward along the spiral axis (e.g., in a direction toward the manipulator magnet 112). Thus, as the cochlear implant advances into and spirals around the spiral axis 122 of the cochlea, a small amount of attractive magnetic force between the manipulator magnet and magnetic element can help to guide the tip of the cochlear implant (toward the manipulator magnetic) in the spiral of the cochlea. Attractive or repulsive magnetic force can be generated by having the magnetic axis 118 of the manipulator magnet slightly deviate from a 90 degree angle to the magnetic axis 124 of the magnetic element 110 to produce a desired amount of magnetic force. For example, angle 126 can be greater than or less than 90 degrees, such as for example between about 85 and about 95 degrees, between about 80 and about 100 degrees, and between about 70 and about 110 degrees. The resulting magnetic force can be, for example, within a range of about 0.027 N to about 5.9 N.

Thus, insertion of the cochlear implant 108 can include simultaneously advancing the cochlear implant using the positioner 106, rotating the manipulator magnet 112 to bend the cochlear implant around the spiral axis 122, and maintaining the magnetic axis 118 at a desired angle relative to the magnetic axis 124. As noted above, the desired angle between the magnetic axis 118 and magnetic axis 124 can be approximately 90 degrees, or within a desired range of angles. The magnetic axis of the manipulator magnet can lead or lag the magnetic axis of the magnetic element.

If desired, the amount of magnetic torque and magnetic force produced on the magnetic element 110 can be varied by moving the rotatable manipulator magnet 112 closer to or further away from the cochlea 102. Accordingly, if desired, the system 100 can also include a means for linearly positioning the magnetic source means. For example, the system 100 can include a second positioner (see FIG. 3, described further below) coupled to the rotatable manipulator magnet to provide for linear positioning of the manipulator magnet. The second positioner can thus be controlled to move the rotatable manipulator magnet toward and away from the cochlea (e.g., along rotation axis 114 of the manipulator magnet). Thus, the insertion of the cochlear implant can also include simultaneously advancing the cochlear implant, rotating the manipulator magnet, and moving the manipulator magnet. For example, when using a nominally straight cochlear implant, as the implant is inserted further into the cochlea, the rotatable manipulator magnet can be moved closer to the cochlea, increasing the torque, helping to overcome increased mechanical restoring stress present as the cochlear implant is bent into a larger spiral. As another example, when using a precurved cochlear implant, the rotatable manipulator magnet may initially be positioned close to the cochlea, and then moved away as the implant is inserted further into the cochlea, reducing torque and allowing the implant to return to its precurved shape.

Because the magnetic field of a source is homothetic, but field gradient is not, differing balances of magnetic force and magnetic torque can be obtained by scaling the size of the rotatable manipulator magnet and the distance from the rotatable manipulator magnet from the cochlear implant. For example, for a magnet of linear dimension n, the dipole strength scales as $n^3$. However, if distance from the magnetic is also scaled by n, we find that field strength remains constant at the scaled distance. Field gradient, however, scales as $1/n$ at the scaled distance. Thus, magnetic force can be decreased while maintaining constant torque by increasing the size of the manipulator magnet and moving the manipulator magnet further away from the cochlear implant.

Varying the angle 126 between the manipulator magnet's magnetic axis 118 and the magnetic element's magnetic axis 124 can also prove helpful. For example, a small amount of dither can be superimposed onto the rotation of the manipulator magnet 112. The dithering can include small and large positive and negative variations of the angle from the desired (nominal) angle. For example, plus and minus variations of up to 5 degrees, up to 10 degrees, or even up to 90 degrees can be used. The dithering can cause vibration or wiggling of the cochlear implant 108 during insertion which can help to reduce stick-slip forces. The dithering can also result in propagating mechanical waves along the length of the cochlear implant that may assist in helping the cochlear implant to move forward (e.g., provide a crawling action) within the cochlea 102. Dithering can be performed at various frequencies, including for example dithering at a rate between 0.5 Hertz and 20 Hertz.

If desired, the magnetic element 110 at the tip 107 of the cochlear implant 108 can be removable. Accordingly, after complete insertion of the cochlear implant, the magnetic element can be detached and withdrawn from the cochlea 102. For example, a small wire can be connected to the magnetic element and used to withdraw the magnetic element. If desired, steering of the magnetic element during withdrawal can also be performed in a similar manner as during insertion. Of course, with the magnetic element detached from the cochlear implant, much smaller torque can be sufficient to control orientation of the magnetic element.

The positioner 106 can also include a force sensor (not shown) to monitor insertion force applied to the cochlear implant 108. The force sensor can be coupled to the control subsystem 120 to allow monitoring of insertion force on the cochlear implant during insertion. For example, during insertion the force sensor can be monitored to determine if the insertion force exceeds a predefined threshold. For example, a threshold can be between 0.03 N and 1.0 N Excessive insertion force (e.g., insertion force greater than threshold) can be indicative of misalignment, incorrect angle, sticking, or other problems. If desired, when excessive insertion force is detected, corrective action can be taken including any of: completely or partially withdrawing the cochlear implant, changing the angle of the magnetic element, starting or ending dithering, increasing or decreasing dithering amplitude or frequency, changing relative angles of the magnetic axes, or the like.

Figure 3:
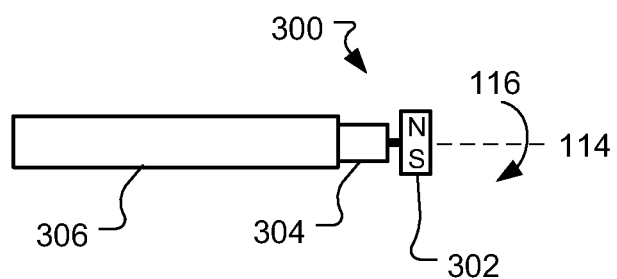
FIG. 3 is a schematic block diagram of a rotatable manipulator magnet mounted on a positioner in accordance with some embodiments of the present invention.

FIG. 3 provides a detailed example of one embodiment of a rotatable manipulator magnet 300, which can be used as rotatable manipulator magnet 112. The rotatable manipulator magnet can include a permanent magnet 302 which can be coupled to a rotator 304. The permanent magnet can be, for example, an axially or diametrically magnetized element. The rotator can provide rotation of the permanent magnet, for example, by coupling the permanent magnet to a drive shaft of the rotator. The rotator can be, for example, a rotary actuator, a motor, or the like.

If desired, the rotatable manipulator magnet 300 can be mounted to a positioner 306. The positioner can provide a second positioning means for linear positioning of the rotatable manipulator magnet.

Figure 4:
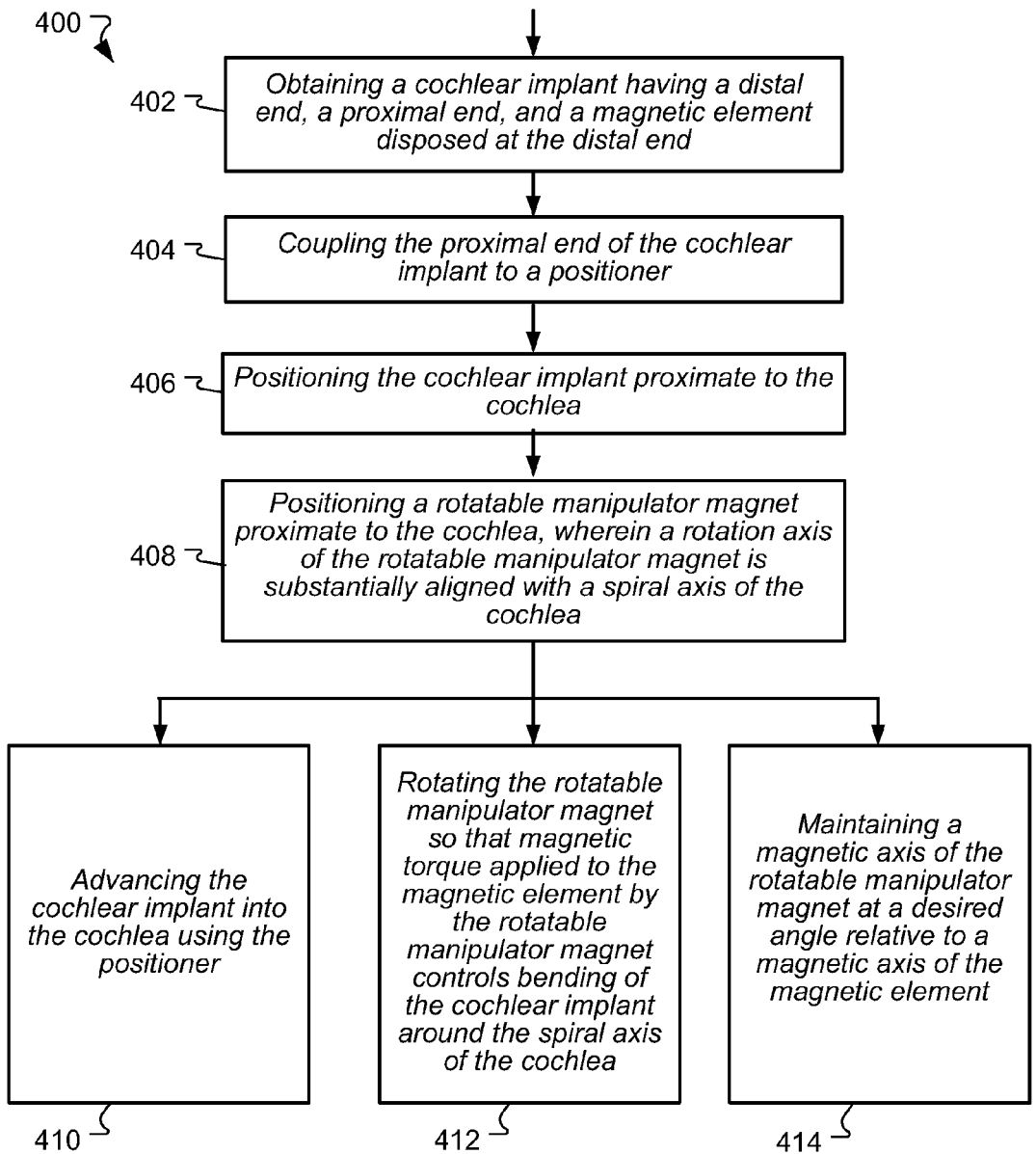
FIG. 4 is a flow chart of a method of inserting a cochlear implant into a cochlea in accordance with some embodiments of the present invention.

Referring to FIG. 4, a flow chart of a method 400 of inserting a cochlear implant into a cochlea is disclosed. The method can include obtaining 402 a cochlear implant. For example, the cochlear implant can be purchased from a supplier of cochlear implants. As another example, the cochlear implant can be manufactured. Obtaining the cochlear implant can include preparing the cochlear implant for use, including for example, sterilizing the cochlear implant. The cochlear implant can include a proximal end and a distal end, and a magnetic element can be disposed at the distal end.

The method 400 can include coupling 404 the proximal end of the cochlear implant to a positioner, positioning 406 the cochlear implant proximate to the cochlea, and positioning 408 a rotatable manipulator magnet proximate to the cochlea. A rotation axis of the rotatable manipulator magnetic can be positioned so that a rotation axis of the rotatable manipulator magnetic is substantially aligned with a spiral axis of the cochlea.

The method 400 can also include simultaneously performing operations 410, 412 and 414. The cochlear implant can be advanced into the cochlea using the positioner while rotating the rotatable manipulator magnet and maintaining a magnetic axis of the rotatable manipulator magnet at a desired angle to control bending of the cochlear implant. The bending can be controlled around the spiral axis of the cochlea to provide the desired amount of curvature of the cochlear implant. As described above, the bending can be controlled by magnetic torque applied by the magnetic element. The desired angle can include dithering, for example as described above. The positioner can be actuated to advance the cochlear implant into the ear. The positioner can be used to linearly translate the cochlear implant in a direction aligned with a longitudinal axis of the cochlear implant. If desired, the cochlear implant can be mounted at an angle relative to the translation axis of the positioner.

If desired, the method 400 can include moving the rotatable manipulator magnet in a direction along the spiral axis of the cochlea (i.e., toward or away from the cochlear implant) simultaneously with operations 410, 412, and 414. For example, moving the manipulator can allow for increase or decrease of magnetic forces as described above.

If desired, the method 400 can include removing the magnetic element from the cochlea after operations 410, 412 and 414 have been completed and the cochlear implant has been inserted to the desired depth. While withdrawing the magnetic element, steering can continue to be performed, if desired, to help reduce contact between the magnetic element and the walls of the cochlea.

Figure 5:
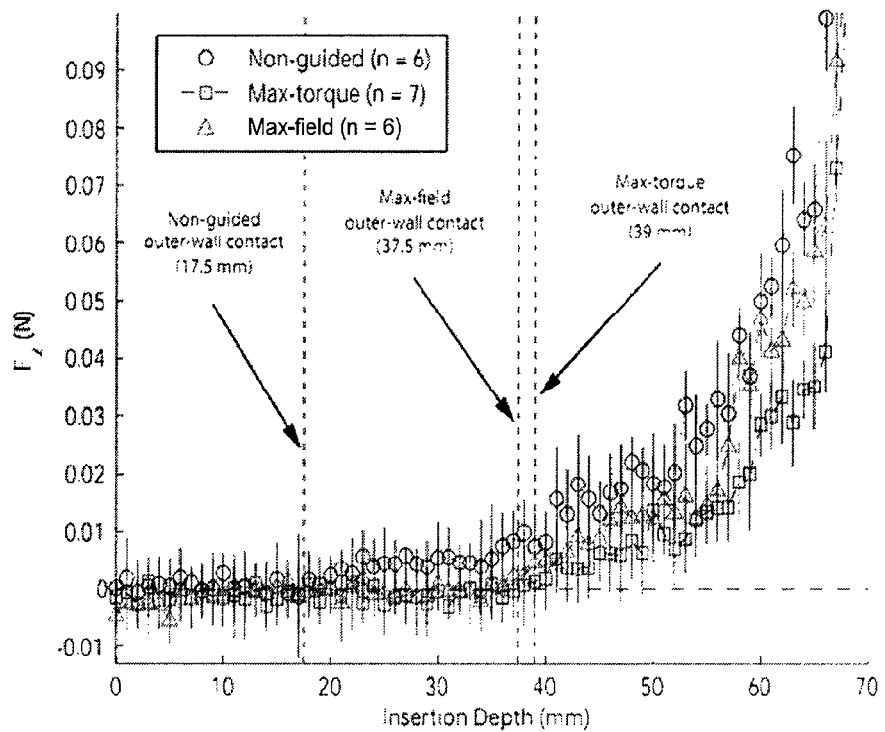
FIGS. 5-6 are graphs showing insertion force versus insertion distance comparing various embodiments of the present invention to non-guided insertion.
Figure 6:
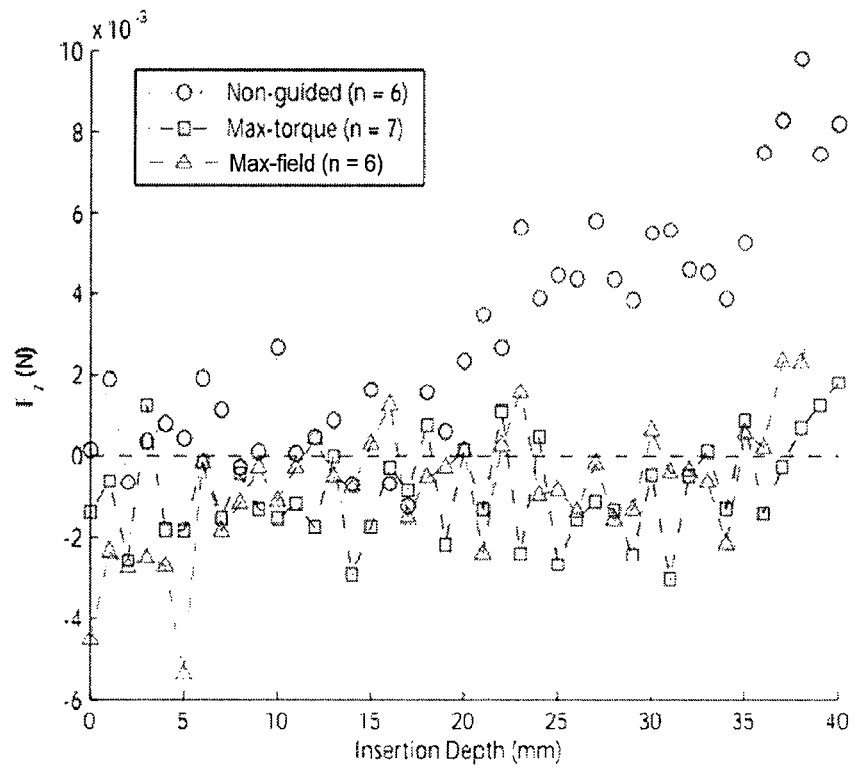

FIGS. 5 and 6 provide experimental results that were obtained using a three-times scaled model of a simulated cochlear implant and scaled model of a human scala-tympani. Shown in the vertical axis is the insertion force measured at the base of the cochlear implant in the direction along the longitudinal axis of the implant. The insertion force is shown as a function of the insertion depth in the horizontal axis. FIG. 5 shows insertion force over the range of 0 to 66 mm, at which point insertion forces increased rapidly (this corresponds to insertion of approximately 490 degrees of spiral). FIG. 6 is an enlargement of the data from FIG. 5 over the range of 0 to 40 mm.

Multiple measurements were obtained for each point and averaged to yield the plotted values along with two-sigma confidence indicators (solid vertical lines). Measurements were performed for three different techniques: non-guided (circles), maximum torque steering (squares), and maximum force steering (triangles). In general, it can be seen the maximum force steering provides reduced insertion forces as compared to non-guided, and maximum torque steering provides even lower insertion forces as compared to either maximum force steering or non-guided. Reduced insertion forces are expected to correspond to reduced damage during the insertion process.

Vertical dashed lines show the points of first contact with the outer wall of the scala-tympani model. It can be seen that the contact with the outer wall does not occur until much later in the insertion process when using magnetic steering, also helping to reduce potential damage. Moreover, it has been observed that, even after the cochlear implant makes contact with the outer wall, the tip can be angled inward so that it is directed away from the wall. This can help the tip to slide along the wall rather than dig into and puncture the wall.

While the foregoing examples have been described exclusively with respect to inserting a cochlear implant into the cochlea, the presently disclosed technique may find application in other areas. For example, the presently disclosed technique may be applied to insertion of other elongate structures into curved channels.

Use of the currently disclosed techniques can provide for deeper insertion of cochlear implants into the cochlea, which can enable improved low-frequency hearing response for a cochlear implant system. Use of the currently disclosed techniques can also provide for reduced intracochlear damage during the insertion, helping to preserve residual hearing and avoid degradation of cochlear implant system effectiveness. Use of the currently disclosed techniques can also provide for improved modiolar proximity of the inserted cochlear implant.

While several illustrative applications have been described, many other applications of the presently disclosed techniques may prove useful. Accordingly, the above-referenced arrangements are illustrative of some applications for the principles of the present invention. It will be apparent to those of ordinary skill in the art that numerous modifications can be made without departing from the principles and concepts of the invention as set forth herein. Accordingly, the following preliminary claims are presented merely as examples, and not by way of limitation, of what the inventors consider as their invention.

The invention claimed is:

1. A system for insertion of a cochlear implant into a cochlea, the system comprising:
    a cochlear implant having a magnetic element;
    a positioner removably attached to a proximal end of the cochlear implant, the positioner being configured to mechanically move the cochlear implant to provide linear positioning of the cochlear implant within the cochlea;
    a rotatable manipulator magnet configured to provide a rotatable magnetic field, the rotatable manipulator magnet having north and south magnetic poles defining a single magnetic axis, wherein the rotatable manipulator magnet is rotatable about a rotation axis perpendicular to the magnetic axis; and
    a control subsystem coupled to the positioner and to the rotatable manipulator magnet, the control subsystem being configured to coordinate linear movement of the cochlear implant with rotation of the manipulator magnet to maintain a magnetic axis of the manipulator magnet at a desired angle relative to a magnetic axis of the magnetic element.

2. The system of claim 1, further comprising a second positioner configured to mechanically move the rotatable manipulator magnet to provide linear positioning of the rotatable manipulator magnet.

3. The system of claim 1, where the rotatable manipulator magnet comprises:
    a rotator; and
    a permanent magnet coupled to said rotator.

4. The system of claim 1, where the rotatable manipulator magnet comprises an electromagnet.

5. The system of claim 1, wherein the cochlear implant includes a single magnetic element.

6. The system of claim 5, wherein the single magnetic element is disposed at a distal end of the cochlear implant.

7. The system of claim 1, wherein the rotatable manipulator magnet is a single magnetic element.

8. The system of claim 1, wherein the magnetic element comprises a permanent magnet.

9. The system of claim 1, wherein the rotatable manipulator magnet is a permanent magnet.

10. The system of claim 1, wherein the magnetic axis of the rotatable manipulator magnet leads the magnetic axis of the magnetic element.

11. The system of claim 1, wherein the rotatable manipulator magnet creates a non-uniform magnetic field in an immediate vicinity of the magnetic element.

12. The system of claim 1, wherein a magnitude of torque produced on the magnetic element by the rotatable manipulator magnet is within the range of about 0.27 Newton-mm to about 58.8 Newton-mm.

13. The system of claim 1, wherein a magnitude of force produced on the magnetic element by the rotatable manipulator magnet is less than about 0.027 Newton.

14. The system of claim 1, wherein the magnetic element maintains a magnetic field in the presence of the rotatable magnetic field.

15. A system for insertion into a cochlea of a cochlear implant having a magnetic element, the system comprising:

a positioning means for linearly positioning the cochlear implant in a direction substantially aligned with a longitudinal axis of the cochlear implant, the positioning means being removably attached to a proximal end of the cochlear implant and configured to mechanically move the cochlear implant;

a source means for generating a rotatable magnetic field originated from a localized source relative to the cochlea, the source means having north and south magnetic poles defining a single magnetic axis, wherein the source means is rotatable about a rotation axis perpendicular to the magnetic axis; and a rotation means for rotating the rotatable magnetic field wherein a magnetic torque applied to the magnetic element of the cochlear implant controls bending of the cochlear implant around the spiral axis of the cochlea while simultaneously maintaining a magnetic axis of the rotatable magnetic field at a desired angle relative to a magnetic axis of the magnetic element to maintain a desired magnetic force on the magnetic element.

16. The system of claim 15, wherein the source means comprises a localized source of magnetic field.

17. The system of claim 15, wherein the source means produces a magnetic field having a non-uniform magnitude.

18. The system of claim 15, further comprising a second positioning means for linearly positioning the source means, the second positioning means being configured to mechanically move the source means.

* * * * *